United States Patent [19]

Belluzzi

[11] Patent Number: 5,234,945

[45] Date of Patent: Aug. 10, 1993

[54] METHOD OF PRODUCING BODY WEIGHT AND FOOD INTAKE USING A DOPAMINE D2 RECEPTOR AGONIST

[75] Inventor: James D. Belluzzi, Irvine, Calif.

[73] Assignee: Whitby Research, Inc., Richmond, Va.

[21] Appl. No.: 641,221

[22] Filed: Jan. 4, 1991

Related U.S. Application Data

[63] Continuation of Ser. No. 349,091, May 9, 1989, abandoned.

[51] Int. Cl.$^5$ .................... A61K 31/38; A61K 31/135
[52] U.S. Cl. .................... 514/438; 514/657; 514/910
[58] Field of Search .................... 514/438, 657, 910

[56] References Cited

U.S. PATENT DOCUMENTS 4,564,628 1/1986 Horn .................... 514/438

FOREIGN PATENT DOCUMENTS 41488 12/1981 European Pat. Off. ............ 514/657

OTHER PUBLICATIONS

Rusk, Chemical Abstracts vol. 110, 1989, Abstract 108007m.

Primary Examiner—Mukund J. Shah
Assistant Examiner—E. C. Ward
Attorney, Agent, or Firm—Richard J. Hammond

[57] ABSTRACT

This invention provides a method for treating the symptoms of obesity which comprises administering to a human or other mammal suffering from the symptoms of obesity an effective amount of a compound selected from the group consisting of the optically active compounds especially the (−) negative stereoisomers represented by the formula:

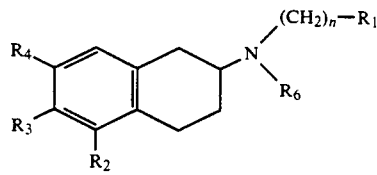

wherein $R_1$ $R_2, R_3, R_4, R_5$ and $R_6$ are defined by the specification substituted or unsubstituted phenyls, pyridyl, hydroxyphenyl,

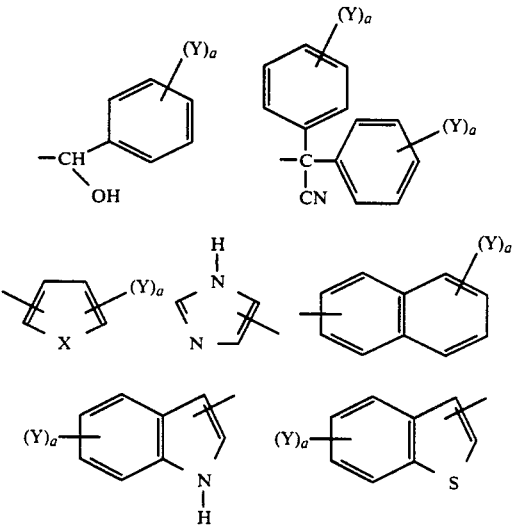

X is oxygen or sulfur, Y is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from zero to 3, $R_2$, $R_3$ and $R_4$ are each selected from the group con- (Abstract continued on next page.)

sisting of H and OA, A is H or is selected from the group consisting of hydrocarbyl radicals, $R_5$ is selected from the group consisting of hydrocarbyl radicals; n is an integer between 1 and 3; and $R_6$ is an alkyl chain having between 1 and 3 carbon atoms with the provision that at least one of $R_2$, $R_3$ and $R_4$ is H, that at least one of $R_2$, $R_3$ and $R_4$ is not H, and that $R_2$ and $R_4$ are not both OA, and pharmaceutically acceptable salts thereof. Preferably, $R_2$ is oxygen.

Most preferably, $R_2$ is OA and A is H, and the compound is the (−) isomer.

3 Claims, 4 Drawing Sheets

N = 5 FOR ALL GROUPS
⊠ = FOOD-DEPRIVED BEFORE IMPLANT AT DAY 3 (200 μl/hr)
△ = DATA FROM EXPERIMENT 2, FIGURE 2 FOR COMPARISON

METHOD OF PRODUCING BODY WEIGHT AND FOOD INTAKE USING A DOPAMINE D2 RECEPTOR AGONIST

This application is a continuation, of application Ser. No. 07/349,091, filed May 9, 1989, now abandoned.

FIELD OF INVENTION

This invention relates to compositions comprising a dopaminergic agent and to a method for administering said compositions in an amount effective to induce anorexia and weight loss in the body of a human or animal.

INTRODUCTION

The search for drugs useful as diet aids is ongoing. The amphetamines have been enlisted for the purpose of inducing weight loss, but their undesirable side effects include restlessness, irritability, and panic, among others. Moreover, it has been found that weight loss induced by amphetamines in obese humans is due almost entirely to reduced food intake, rather than to increased metabolism, and tolerance to accepted doses develops rapidly (Goodman, L. S., *The Pharmacological Basis of Therapeutics*, 7th Ed., MacMillan, New York, 1985, pp. 166-67).

Dopamine systems in the central nervous system have long been implicated in the anorexic effects of stimulant drugs such as amphetamine. Direct tests of dopaminergic involvement have become possible with the discovery of more specific dopamine agonists. Anorexia was produced in rats given dopamine agonists such as lisuride, lergotrile and bromocriptine (Carruba, M. O., Ricciardi, S., Muller, E. E. and Mantegassa, P., "Anorectic effect of lisuride and other ergot derivatives in the rat," *Eur. J. Pharmacol.* 64:133-141, 1980.) More recently a related dopamine agonist, pergolide was shown to induce anorexia in rodents, but repeated administration produced tolerance to the anorexic effects (Greene, S. B., Mathews, D., Hollingsworth, E. M. and Garbin, C. P., "Behavioral effects of pergolide mesylate on food intake and body weight," *Pharmac. Biochem. Behav.* 23:161-167, 1985.)

The role of specific dopamine receptor subtypes in the anorexic actions of dopamine agonists has been studied recently. For instance, amphetamine-induced anorexia was blocked by the selective dopamine D1 receptor antagonist SCH 23390, but not by the selective D2 receptor antagonist sulpiride. This discovery suggests that amphetamine produces . anorexia by stimulation of the dopamine D1 receptor (Gilbert, D. B. and Cooper, S. J., "Analysis of dopamine D1 and D2 receptor involvement in d- and l-amphetamine-induced anorexia in rats," *Brain Res. Bull.* 15:385-389, 1985.) However, Rusk, I. and Cooper, S. J. ("Dopamine D1 and D2 receptors in relation to palatable food consumption in the rat," *Soc. Neurosci. Abst.* 12:1557, 1986) reported anorexic effects following administration of selective dopamine D2 receptor agonists RU24213 and N-0437. Furthermore, it has been found that the anorexic effects of N-0437 are completely antagonized by the selective D2 antagonist, YM-09151-2 (Rusk, I. N. and Cooper, S. J., "Profile of the selective dopamine D-2 receptor agonist N-0437: its effect on palatability- and deprivation-induced feeding, and operant responding for food," *Physiol. Behav.* 44:545-553, 1988.) In support of the hypothesis that D2 receptors play a role in anorexia, it was recently reported that sulpiride, a D2 receptor antagonist, but not SCH 23390, a D1 receptor antagonist, blocks anorexia produced by apomorphine (Towell, A., Willner, and Muscat, R., "Apomorphine anorexia: the role of dopamine receptors in the ventral forebrain," *Psychopharmacology* 96:135-141, 1988.)

However, the ability of compounds known to produce temporary loss of appetite in an animal to which it is administered does not necessarily predict that sustained weight loss can be achieved in animals or humans to which the same drug is administered over a period of weeks. The temporary anorexia induced in an animal during a 30-minute feeding test, for instance, does not predict whether the animal will experience a rebound effect as soon as the drug wears off such that food consumption over a 24-hour period is the same with or without administration of the drug despite a brief period of drug-induced reduced food intake.

In addition, although it is known that for many dopamine D2 agonists on stereoisomer will generally have considerably greater potency in reducing food intake, no studies have been conducted to determine which isomer induces the greatest weight loss.

The need exists for more and better drugs useful in the treatment of obesity in humans and other animals. Especially, the need exists for drugs that cause a minimum of undesirable side effects at therapeutic dosages and for drugs that do not show tolerance in the subject upon prolonged administration, but are capable of inducing sustained weight loss without a rebound effect upon their withdrawal.

SUMMARY OF THE INVENTION

This invention provides a method for inducing anorexia and weight loss in mammals, e.g., humans, which comprises administering to a mammal suffering from obesity an effective amount of a compound selected from the group of optically active compounds represented by the general formula:

wherein $R_1$ is selected from the group consisting of methyl, substituted or unsubstituted phenyls, pyridyl, hydroxyphenyl, X is oxygen or sulfur, Y is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from zero to 3, $R_2$, $R_3$ and $R_4$ are each selected from the group consisting of H and OA, A is H or is selected from the group consisting of hydrocarbyl radicals, $R_5$ is selected from the group consisting of hydrocarbyl radicals; n is an integer between 1 and 3; and $R_6$ is an alkyl chain having between 1 and 3 carbon atoms with the provision that at least one of $R_2$, $R_3$ and $R_4$ is H, that at least one of $R_2$, $R_3$ and $R_4$ is not H, and that $R_2$ and $R_4$ are not both OA, except that when R is meta-hydroxyphenyl, phenyl, or 2-thienyl, the compound is optically active and pharmaceutically acceptable salts thereof. Preferably, $R_2$ is oxygen.

It is essential that the compound selected for use in the method of the present invention be an optically active compound or mixture thereof capable of selectively activating either the postsynaptic or the presynaptic D2 dopamine receptor, e.g., in a human. In particular, it is found that the (+) and (−) enantiomers of 5-hydroxy-2-(N-n-propyl-N-2-[2-thienyl] ethylamino)-tetralin are especially preferred for use in the methods of inducing anorexia and weight loss of the present invention.

DETAILED DESCRIPTION OF THE INVENTION

The compounds used in the present invention are selected from the group of stereoisomers or mixtures thereof of compounds represented by the general formula:

wherein $R_1$ is selected from the group consisting of organic radicals methyl, substituted or unsubstituted phenyls, pyridyl, hydroxyphenyl, X is oxygen or sulfur, Y is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from 0 to 3, $R_2$, $R_3$ and $R_4$ are each selected from the group consisting of H and OA, A is H or is selected from the group consisting of hydrocarbyl radicals, $R_5$ is selected from the group consisting of hydrocarbyl radicals; n is an integer between 1 and 3; and $R_6$ is an alkyl chain having between 1 and 3 carbon atoms with the provision that at least one of $R_2$, $R_3$ and $R_4$ is H, that at least one of $R_2$, $R_3$ and $R_4$ is not H, and that $R_2$ and $R_4$ are not both OA, except that when $R_1$ is meta-hydroxyphenyl, phenyl, or 2-thienyl, the compound is optically active and pharmaceutically acceptable salts thereof. Preferably, $R_2$ is oxygen.

A is preferably H or is selected from the group consisting of phenyl and alkyl radicals having from 1 to 12 carbon atoms, and more preferably $R^5$ is an alkyl or aryl radical that would serve to extend the activity of the compound in the body, for example phenyl, methyl t-butyl, d-methylphenyl, o-, m- or p-methoxyphenyl, or nonyl.

The more preferred groups represented by $R_1$ are thienyl, phenyl, hydroxyphenyl, furanyl and naphthalenyl, e.g., 2-thienyl, 3-thienyl, 3-hydroxyphenyl, 4-hydroxyphenyl, etc.

In the more preferred compounds for use in the present invention n is 2 and $R_2$ is OA; and most preferably A is H and $R_6$ is propyl.

In one embodiment of the invention, the compound selected for use in the method of inducing anorexia and weight loss is an optically active compound or mixture thereof capable of substantially activating the postsynaptic dopamine D2 receptor, e.g., in a human. It has been found that the negative isomers of the claimed compounds possess the ability to predominately stimulate postsynaptic D2 dopamine receptors. As is shown in the Examples hereafter, the (−) isomers are unexpectedly more potent than the positive isomers for inducing anorexia and long term weight loss. A loss of as much as 12 percent of body weight has been achieved by administering a (−) isomer. However, at high dosages, for example, 3 mg/kg, the (−) isomers have been found to induce undesirable side effects of the central nervous system, such as stereotypy in rats.

In particular it has been found that the (−) isomer of 5-hydroxy-2-(N-n-propyl-N-2-[2-thienyl]ethylamino)-tetralin is especially preferred for use in the method of the present invention because the (−) isomer is a strong agonist at postsynaptic receptors and possesses unexpectedly high potency for inducing anorexia and weight loss. U.S. patent application Ser. No. 206,193 filed Jun. 13, 1988,.entitled "Method and Compositions for Treatment of Parkinsonism Syndrome in Mammals," which is hereby incorporated by reference in its entirety, discloses tests showing the preferential stimulation of postsynaptic dopamine D2 receptors by the (−) isomer of compounds used in the present invention.

In another embodiment of the invention, the positive (+) isomers of the compounds disclosed herein are preferred in the method of inducing anorexia and weight loss because at therapeutic doses the (+) isomers produce fewer side effects showing undesirable central nervous system involvement, such as stereotypy in rats. This freedom from side effects persists at dosages ten times as high as the effective dose for the (−) isomer. The (+) isomers of the compounds of the invention are known to be more efficacious at presynaptic than at postsynaptic D2 dopamine receptors and while not wishing to be bound by theory, it is believed that the (+) isomers produce no side effects at the dosages preferred herein because they act preferentially at presynaptic D2 dopamine receptor sites or at a different subset of postsynaptic receptors than do the (−) isomers. It should be remembered, however, that the (+) isomers require a dosage much higher than that required to achieve comparable weight loss using the (−) isomer, i.e, more than ten times as much (+) isomer is required as is needed for comparable result if the (−) isomer is employed.

Thus, the embodiment of the invention employing the (+) isomer should be practiced when it is practical to administer a higher effective dosage of dopaminergic compound to achieve the advantage of avoiding the risk of side effects to the central nervous system. It is preferred that the (+) isomer of 5-hydroxy-2-(N-n-propyl-N-2-[2-thienyl]ethylamino)tetralin be employed to achieve anorexia and weight loss without danger of producing side effects at high dosage.

The above compounds may be made by any of the methods disclosed in U.S. Pat. No. 4,564,628 entitled "Substituted 2-Aminotetralins," which is hereby incorporated by reference. A method for resolving the compounds into (+) and (−) isomers is disclosed in Example 1 hereinafter.

For purposes of this invention, designation of the (−) isomer shall mean that the (−) isomer is present in excess of the (+) isomer. preferably, the mixture is greater than 90 mole percent of the (−) isomer. Most preferably, the (−) isomer is substantially pure, i.e., greater than 99 mole percent. Designation of the (+) isomer is defined by inverse analogy, i.e., most preferably the (+) isomer is substantially pure., i.e, greater than 99 mole percent.

In one group of compounds, $R_1$ is selected from the group consisting of radicals represented by the general formula:

wherein X is oxygen or sulfur. Specific preferred compounds of this group include:

2-(N-n-propyl-N-2-[2-thienyl]ethylamino)-5-hydroxytetralin,
2-(N-n-propyl-N-2-[3-thienyl]ethylamino)-5-hydroxytetralin,
2-(N-n-propyl-N-2-[2-furanyl]ethylamino)-5-hydroxytetralin,
2-(N-n-propyl-N-2-[3-furanyl]ethylamino)-5-hydroxytetralin,
2-(N-n-propyl-N-2-[2-thienyl-4-methyl]ethylamino-5-hydroxytetralin,
2-(N-n-propyl-N-2-[2-thienyl-3,4,5-trimethyl]ethylamino)-5-hydroxytetralin,
2-(N-n-propyl-N-2-[2-thienyl-5-chloro]ethylamino)-5-hydroxytetralin,
2-(N-n-propyl-N-2-[2-(4-bromo-5-methyl)thienyl]ethylamino)-5-hydroxytetralin,
2-(N-n-propy-1-N-2-[2-(4-methyl-5-ethyl)thienyl]ethylamino)-5-hydroxytetralin,
2-(N-n-propyl-N-2-[2-benzothienyl]ethylamino)-5-hydroxytetralin and
2-(N-n-propyl-N-2-[3-benzothienyl]ethylamino)-5-hydroxytetralin.

In a second group of compounds, $R_1$ is selected from the group of radicals represented by the general formulae:

wherein Y and a are as defined above. More preferably, Y comprises no more than 5 carbon atoms and a is 0 or 1 Specific preferred compounds of this group include:

2-(N-n-propyl-N-2-[2-naphthalenyl]ethylamino)-5-hydroxytetralin, 2-(N-n-propyl-N-2-[4-indolyl]ethylamino)-5-hydroxytetralin, 2-(N-n-propyl-N-2-[2-benzothienyl]ethylamino)-5-hydroxytetralin, and 2-(N-n-propyl-N-2-[3-benzothienyl]ethylamino)-5-hydroxytetralin;

In yet another group of compounds, $R^1$ is phenyl and/or substituted phenyl and is selected from the group of radicals represented by the general formula:

wherein Y and a are as defined above. Specific preferred compounds of this group include:

2-(N-n-propyl-N-2-[phenyl]ethylamino)-5-hydroxytetralin, 2-(N-n-propyl-N-2-[4-hydroxyphenyl]ethylamino)-5-hydroxytetralin, and 2-(N-n-propyl-N-2-[3-hydroxyphenyl]ethylamino)-5hydroxytetrlin;

This invention provides a method of treatment of the symptoms of obesity by inducing anorexia and weight loss, which method comprises administering a therapeutically effective amount of one of the foregoing compounds to a patient suffering such symptoms. Even more preferably, the method of the present invention comprises administering the (−) isomer of 5-hydroxy-2-(N-n-propyl-N-2-[2-thienyl]ethyl-amino)tetralin to a human or other mammal to reduce the symptoms of obesity.

The pharmaceutically effective dose will generally be selected within the above range so as to avoid undesirable side effects to the central nervous system while achieving significant antiobesity effects.

In general, a pharmacologically-effective daily dose can be from 0.01 mg./kg. to 100 mg./kg. per day, bearing in mind, of course, that in selecting the appropriate dosage, in any specific case, consideration must be given to the patient's weight, general health, metabolism, age and other factors which influence response to the drug. A preferred dosage is 0.3 to 3 mg./1 kg. of body weight. A particularly preferred dose is 0.3 mg./kg. per day.

The pharmaceutical composition may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets contain the active ingredient in admixture with non-toxic pharmaceutically acceptable excipients which are suitable for manufacture of tablets. These excipients can be, for example, inert diluents, for example calcium carbonate, sodium carbonate, lactose, calcium phosphate, or sodium phosphate; granulating and disintegrating agents, for example maize starch, or alginic acid; binding agents, for example starch, gelatine, or acacia; and lubricating agents, for example magnesium stearate, stearic acids, or talc. The tablets can be uncoated or they can be coated by known techniques to delay disintegration and adsorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate, or kaolin, or as soft gelatine capsules wherein the active ingredient is mixed with an oil medium, for example archis oil, liquid paraffin, or olive oil.

Aqueous suspensions contain the active compound in admixture with excipients suitable for the manufacture of aqueous suspensions. Such excipients are suspending agents, for example sodium carboxmethylcellulose, methylcellulose, hydroxypropylmethylcellulose, sodium alginate, polyvinylpyrrolidone, gum tragacanth, and gum acacia; dispersing or wetting agents may be naturally-occurring phosphatides, for example lecithin, or condensation products of an alkylene oxide with fatty acids, for example polyoxethylene stearate, or condensation products of ethylene oxide with long chain aliphatic alcohols, for example heptadecethyleneoxy-cetanol, or condensation products of ethylene oxide with partial esters derived from fatty acids and a hexitol, for example, polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives, for example ethyl, n-propyl, or p-hydroxy benzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents may also be present.

Syrups and elixirs may be formulated with sweetening agents, for example glycerol, sorbitol or sucrose. Such formulations may also contain a demulcent, preservative, flavoring and coloring agents. The pharmaceutical compositions may be in the form of a sterile injectable preparation, for example as sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol.

The pharmaceutical compositions may be tableted or otherwise formulated so that for every 100 parts by weight of the composition there are present between 5 and 95 parts by weight of the active ingredient. The dosage unit form will generally contain between about 1 mg. and about 100 mg. of the active ingredient of the formula stated above.

From the foregoing discussion of formulations it is apparent that the compositions of this invention can be administered orally or parenterally. The term parenteral as used herein includes subcutaneous injection, intravenous, intramuscular, or intrasternal injection or infusion techniques, as illustrated in the following examples. The compositions can also be administered transdermally by topical administration to skin and mucosal membranes.

To illustrate the manner in which the invention may be carried out, the following examples are given. It is understood, however, that the examples are for the purpose of illustration and the invention is not to be regarded as limited to any of the specific materials or conditions therein.

EXAMPLE 1

Racemic 2-(N-n-propylamino)-5-methoxytetralin was resolved into its (−) and (+) isomers according to the method of Ten Hoeve and Wynberg (J. Org. Chem. 1985, 50, 4508), using the (+) isomer of 4-(2-chlorophenyl)-5,5-dimethyl-2-hydroxy-1,3,2-dioxaphosphorinane 2-oxide.

6.23 gm. (28.5 mmol) of racemic 2-(N-n-propylamino)-5-methoxytetralin and 7.7 gm. (27.8 mmol) of (+) 4-(2-chlorophenyl)-5,5-dimethyl-2-hydroxy-1,3,2-dioxaphosphorinane 2-oxide were dissolved by warming in 33 ml. of absolute alcohol and 10 ml. of water. The heating was discontinued and the solution was allowed to cool while being stirred. After 15 min., the mixture was filtered off and washed with ether to yield 6.08 gm. of the salt (12.27 mmol, 43%). The salt was then stirred 30 min. with a solution of sodium hydroxide dissolved in 75 ml. water to which was added 25 ml. chloroform After mixing, this was extracted with 2×50 ml. portions of chloroform. The organic extracts were washed with water, dried over magnesium sulfate and evaporated to dryness to yield 2.66 gm. (99%) of a slightly colored oil. The optical rotation for 49 mg. in 5 ml. of methanol was −62.4° (578 nm). (The (+) isomer can be similarly isolated by using (−) 4-(2-chlorophenyl)-5,5-dimethyl-2-hydroxy-1,3,2-dioxaphosphorinane 2-oxide.)

The resultant isomers of 2-(N-n-propylamino)-5-methoxytetralin are then converted to (+) and (−) 5-hydroxy-2-(N-n-propyl-N-2-[2-thienyl]ethylamino)-tetralin by the methods described in U.S. Pat. No. 4,564,628 herein incorporated by reference.

EXAMPLE 2

Male albino Sprague Dawley rats obtained from Charles River Labs, Wilmington, Mass. 01887 were used for all in vivo experiments. The animals were placed on a light/dark cycle with lights on from 7:00 a.m. to 7:00 p.m. and water and rat chow were made available ad lib unless otherwise noted. It should be noted that under ad lib conditions these caged animals normally undergo continuous weight gain throughout their adult lives subject only to the limitations of cage size. Therefore, in the following experiments weight loss must be judged against the continuous trend of weight gain the animal would have undergone, as is illustrated in each case by the weight of the vehicle control group.

The effects of the pure stereoisomers of 5-hydroxy-2-(N-n-propyl-N-2-[2-thienyl]ethylamine)tetralin, N-0923 (−) and N-9024 (+), upon food intake and weight gain of the rats were compared with those caused by d-amphetamine sulfate and apomorphine HCl (purchased form Sigma Chemical Co., St. Louis, Mo.)

Animals were maintained in their home cages throughout the experiments and body weight and food intake were measured daily. Animals were weighed to the nearest 0.1 gm using an Ohaus animal balance. Food intake was determined by weighing the food pellets before the feeding session and subtracting the weight of the remaining food pellets plus spillage after the two-hour session using- a Sartorius electronic balance. Drug treatments varied according to the particular experimental procedure as follows:

Experiment 1

Figure 1:
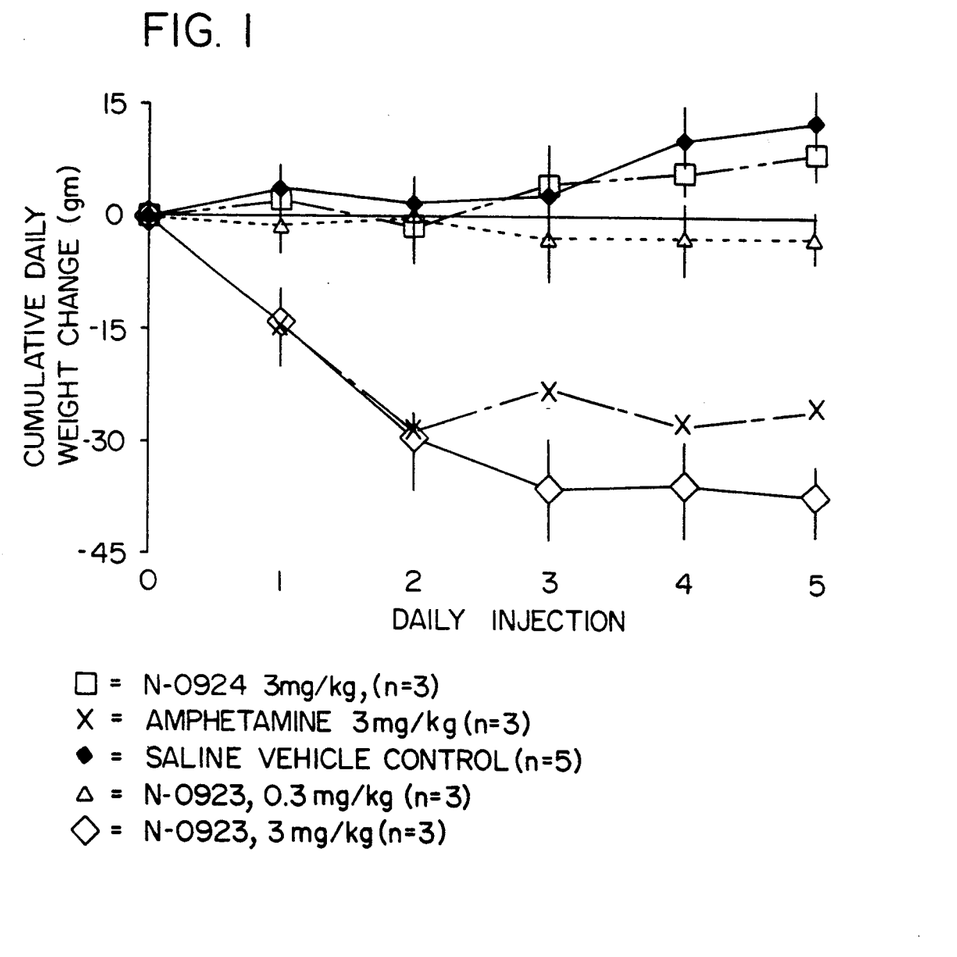
FIG. 1 of the drawing is a graph showing the effects of dopamine agonists on body weight.

Intraperitoneal injections on restricted feeding schedule 24 animals were put on a feeding schedule restricting access to normal lab chow to two hours each day between 14:00 and 16:00 hours. When all animals acclimated to the restricted schedule and food intake and weight gain stabilized, an injection was administered to each animal 30 minutes prior to the daily two hour feeding period. The animals received intraperitoneal injections of one of the following drugs prepared daily: as shown in FIG. 1 N-0923 (0.3 (◊), 1 or 3 (Δ) mg/kg), N-0924 (3 mg/kg (□)), d-amphetamine (X) (3 mg/kg), apomorphine (3 mg/kg) or distilled water vehicle (♦) (1 ml/kg). An individual timer was used for each insure that feeding commenced 30 minutes after the injections and that food was available for two hours. Each animal received 5 consecutive daily injections of one drug at a constant dose. Weight loss for each drug is shown in the difference in weights of the animals administered vehicle control and those of the animals administered the selected drug.

The data summarized in Table 1 show significant reduction of body weight at all doses of N-0923 tested (0.3–3 mg/kg). FIG. 1 shows the same data graphically. Body weight decreased rapidly during the first several days of treatment with N-923, but then the effects appeared to tolerate and the animals' weight stabilized at a lower level. This new weight was maintained for the remainder of the 5-day test period, suggesting that the drug-treated animals were not gaining in a normal manner shown in the vehicle control group weight. Thus, while the anorexic effects appear to tolerate with 3–4 days, the animals did not display any rebound increase in feeding.

The animals receiving the highest dose of N-0923 (3 mg/kg) displayed stereotypic behavior, which might account for the reduced feeding. But it should be noted that the lowest dose of N-0923 (0.3 mg/kg) showed significant weight loss without any measurable stereotypic behavior. The animals receiving a comparable dose of amphetamine also exhibited side effects to the central nervous system including heightened excitability and some symptoms of stereotypy. No stereotypic behavior or other signs of increased nervousness or irritability were noticed in any animals receiving the (+) isomer.

TABLE 1

The effects of dopamine agonists on body weight and food intake

| Drug | Dose (mg/kg) | N | Cumulative Change on Day Five (gm) | |
|---|---|---|---|---|
| | | | Body Weight | Food Intake |
| Vehicle | — | 5 | 12.9 ± 0.8 | −0.1 ± 1.5 |
| N-0923 | 0.3 | 3 | −2.4 ± 2.9+ | −5.9 ± 0.8* |
| N-0923 | 1.0 | 3 | −6.3 ± 1.8++ | −2.3 ± 2.0 |
| N-0923 | 3.0 | 3 | −36.9 ± 4.3++ | −7.6 ± 2.1* |

TABLE 1-continued

| | The effects of dopamine agonists on body weight and food intake | | | |
|---|---|---|---|---|
| Drug | Dose (mg/kg) | N | Cumulative Change on Day Five (gm) | |
| | | | Body Weight | Food Intake |
| N-0924 | 3.0 | 3 | 8.7 ± 3.2 | 1.2 ± 1.7 |
| Apomorphine | 3.0 | 3 | 1.2 ± 5.0* | −0.2 ± 2.3 |
| Amphetamine | 3.0 | 3 | −25.4 ± 1.9* | −6.2 ± 3.1* |

*significantly different from vehicle $p < 0.05$;
¯$p < 0.01$;
¯¯$p < 0.001$

The (−) isomer was slightly more potent than d-amphetamine in producing weight loss, although both produced significant weight loss (Table 1). While considerably less potent than the (−) isomer, N-0924, the (+) isomer, showed a slight trend to produce weight loss. Stereoselectivity of the antiobesity effect of N-0437 is, thus, illustrated by the substantial increase in potency of the (−) isomer over the (+) isomer.

Experiment 2

Continuous 1-week drug infusion on free-feeding schedule

Body weight and food intake were recorded daily for 30 animals maintained on ad lib food and water. When weight and intake measurements had stabilized the animals were divided into treatment groups balanced to achieve equal mean body weights in each group (N=5/group). In the first phase, animals were implanted with Alzet osmotic minipumps (model 2ML1) designed to deliver 10 μl/hour for 1 week.

Figure 2:
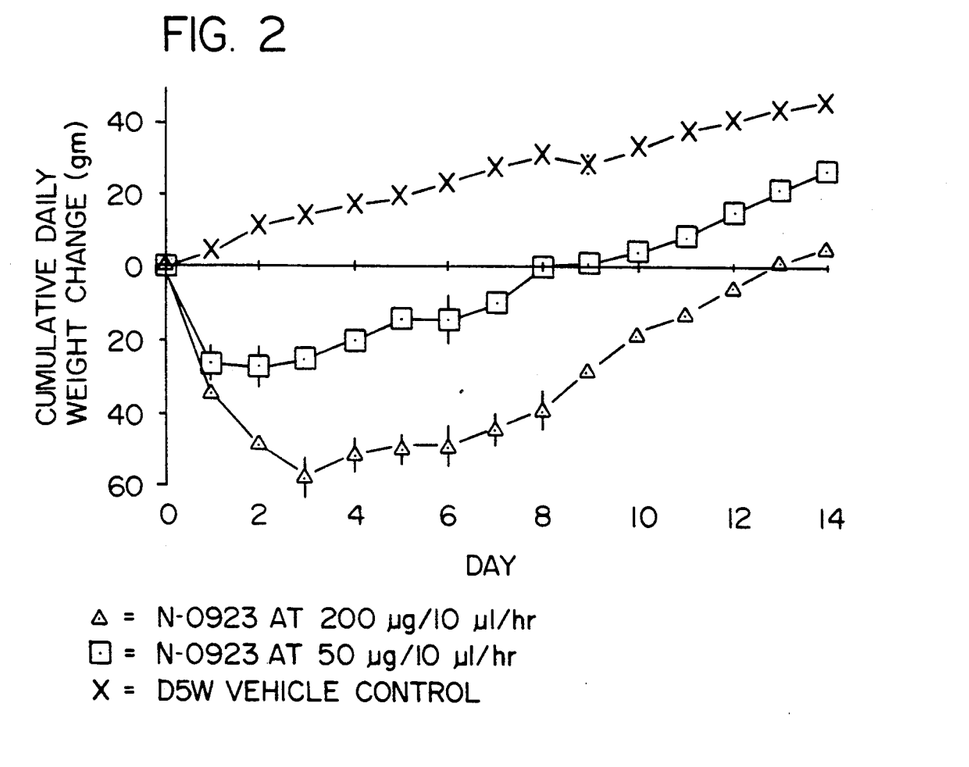
FIG. 2 of the drawing is a graph showing the effect of continuous 24-hour infusion of N-0923 on body weight in free-feeding rats.

Animals were lightly anesthetized with methoxyflurane and a small incision was made on the back of the animal at the level of the shoulders and the pumps were inserted (Δ) with the injection outlet pointed inward. As shown in FIG. 2, three groups of 5 animals received either N-0923 (50 (·) or 200 (·) μg/10 μl) or vehicle (5% dextrose in water (X) at equal rates). In the second phase, 3 additional groups of 5 rats had their food intake restricted to produce weight loss to a starting weight equal to that induced by N-0923 (200 μg/10 μl/hr) in the previous experiment. After 3 days on this feeding schedule, 5 animals received minipump implants containing (N-0923 (200 μg/10 μl/hr). To test the effect of starvation in the above animals, 10 animals representing an unstarved control were allowed to free-feed for 24 hours, at which time they received minipump implants containing either N-0923 (200 μg/μl/hr) or vehicle. All pumps were removed after one week and body weight and food intake measurements were taken for an additional week.

As is shown in the results summarized in FIG. 2, continuous 24-hour infusion of N-0923 (Δ) and (☐) reduced body weight in free-feeding animals at both doses tested. But once again the anorexic effects tolerated after 3-4 days. This shows that the hunger produced by 22-hour food deprivation in Experiment 1 was not responsible for the tolerance. It also shows more clearly that the animals do not regain the lost weight quickly after the drug is removed. As indicated in FIG. 2, the body weights of the drug-treated groups appear to still be slowly converging with those of the vehicle control group 7 days after the drug was removed (day 14).

Figure 3:
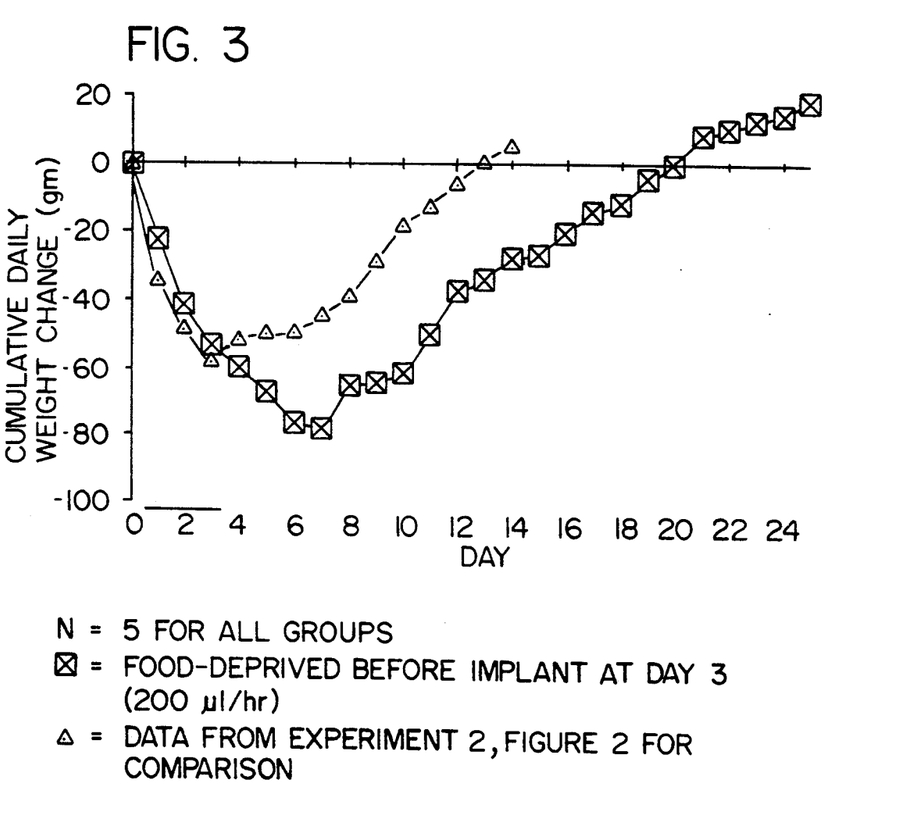
FIG. 3 of the drawing is a graph showing the influence of starting body weight on the anorexic effects of N-0923.

The tolerance of the anorexic effects observed in Experiment 2 did not appear to be due to either the reduced body weight or the state of starvation. FIG. 3 below shows that animals whose body weight had been reduced by food deprivation (☒) to the same degree as that produced by N-0923 (3 mg/kg) (△) nearly identical additional weight loss when the drug was administered In addition, allowing the starved animals to free feed did not alter the drug effect, i.e., weight loss from the deprived body weight was similar to that from the undeprived body weight (data not shown).

Experiment 3

Continuous 4-week drug infusion on free-feeding schedule

Thirty-six animals were treated as in Experiment 2 above except that they received minipumps (2ML4) that delivered drugs at 2.5 μl/hr continuously for 4 weeks. The pumps were loaded with N-0923 (50 μg/2.5 μl/hr), amphetamine 7.15 μg/2.5 μl/hr) or vehicle (5% dextrose in water). Body Weight and food intake measurements were taken for a total of 3 months comprising 1 week prior to pump implantation, 1 month during drug infusion, and 7 weeks after pump removal.

Figure 4:
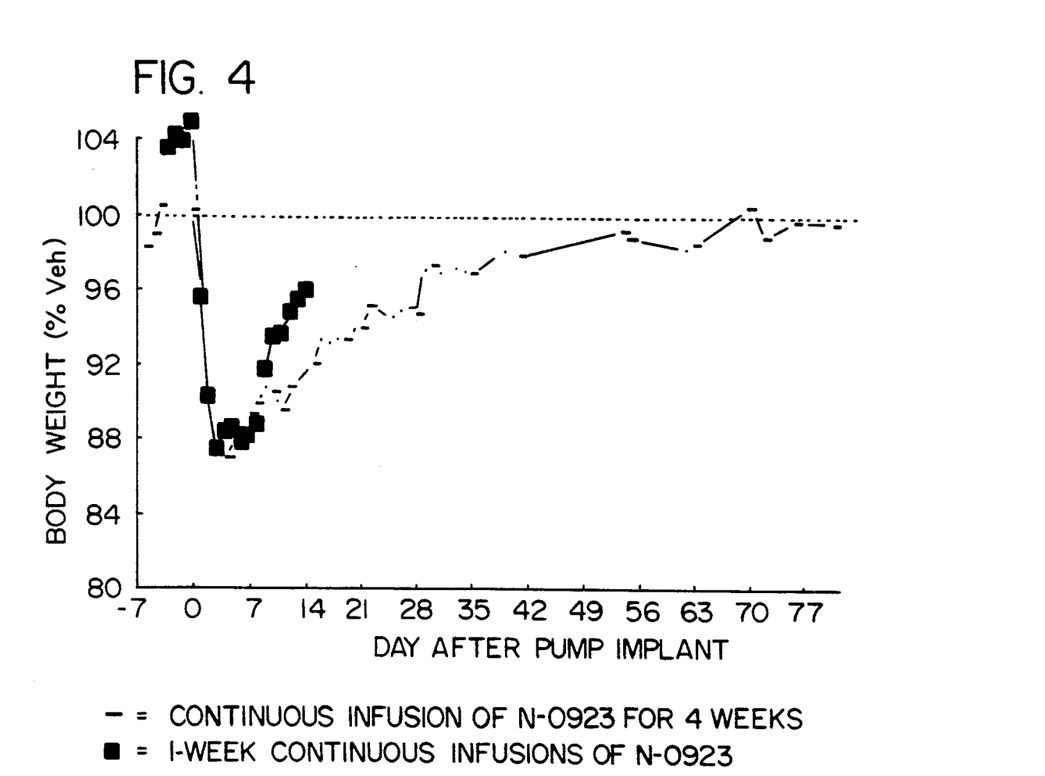
FIG. 4 is a graph comparing affects of 1 week and 4 weeks of continuous infusions of N-0923.

The data summarized in FIG. 4 shows that continuous 24-hour infusion of N-0923 at 50 μg/2.5 μl/hr (-) for 4 weeks maintained a lower body weight than the 1-week treatment of the same drug at the same rate (■). These results show that the drug continued to reduce intake below free-feeding levels and retarded weight gain over the 4-week period in spite of the initial tolerance. After the drug was removed, animals slowly regained body weight over a period of one month until they were equal in weight to vehicle control animals, whose body weight continuously increases due to the effects of captivity.

While particular embodiments of the invention have been described, it will be understood, of course, that the invention is not limited thereto since many obvious modifications can be made and it is intended to include within this invention any such modifications as will fall within the scope of the appended claims.

We claim:

1. A method for inducing anorexia and weight loss in a mammal, comprising administering to said mammal an effective amount of a compound selected from the group consisting of the optically active compounds represented by the formula:

where $R_1$ is thienyl; $R_2$, $R_3$ and $R_4$ are each selected from the group consisting of hydrogen and OA, A is hydrogen or is selected from the group consisting of hydrocarbyl radicals, where $R_5$ is selected from the group consisting of hydrocarbyl radicals; n is an integer between 1 and 3; and $R_6$ is an alkyl chain having between 1 and 3 carbon atoms with the provision that at least one of $R_2$, $R_3$ and $R_4$ is hydrogen, that at least one of $R_2$, $R_3$ and $R_4$ is not hydrogen, and that $R_2$ and $R_4$ are not both OA, and pharmaceutically acceptable salt thereof.

2. The method of claim 1 wherein $R_2$ is OA an A is hydrogen.

3. The method of claim 1 wherein the amount of (−) isomer of 5-hydroxy-2-(N-n-propyl-N-2 ethylamine tetralin is less than about 0.3 mg per Kg of food intake.

* * * * *

UNITED STATES PATENT AND TRADEMARK OFFICE
CERTIFICATE OF CORRECTION

PATENT NO. : 5,234,945
DATED : August 10, 1993
INVENTOR(S) : Belluzzi, James D.

It is certified that error appears in the above-indentified patent and that said Letters Patent is hereby corrected as shown below:

Title page, item [54] and col. 1, line 1, delete "Producing" and insert therein --Reducing--.

Column 14, Claim 3, line 2, between "5-hydroxy-2-(N-n-propyl-N-2" and "ethylamine" insert--[2-thienyl]--; line 2, delete "ethylamine" and insert therein --ethylamine)--.

Signed and Sealed this

Fourteenth Day of February, 1995

Attest:

BRUCE LEHMAN

Attesting Officer

Commissioner of Patents and Trademarks